(12) United States Patent
Dahne et al.

(10) Patent No.: US 11,110,050 B2
(45) Date of Patent: Sep. 7, 2021

(54) HAIR STYLING METHOD AND KIT THEREOF

(71) Applicant: Coty Inc., New York, NY (US)

(72) Inventors: Lars Siegfried Dahne, Berlin (DE); Mathias Kurt Herrlein, Kronberg (DE); Tatjana Schaefer, Butzbach (DE); Judith Hagios, Sulzbach (DE); Mandy Hecht, Falkensee (DE); Moritz Klickermann, Berlin (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

(21) Appl. No.: 16/488,037

(22) PCT Filed: Oct. 5, 2018

(86) PCT No.: PCT/US2018/054706
§ 371 (c)(1),
(2) Date: Aug. 22, 2019

(87) PCT Pub. No.: WO2019/071194
PCT Pub. Date: Apr. 11, 2019

(65) Prior Publication Data
US 2020/0009039 A1     Jan. 9, 2020

(30) Foreign Application Priority Data
Oct. 6, 2017 (EP) .................................. 17195272

(51) Int. Cl.
*A61K 8/81* (2006.01)
*A61K 8/73* (2006.01)
*A61Q 5/06* (2006.01)
(52) U.S. Cl.
CPC ............ *A61K 8/8111* (2013.01); *A61K 8/731* (2013.01); *A61K 8/733* (2013.01); *A61K 8/8117* (2013.01); *A61Q 5/06* (2013.01); *A61K 2800/5424* (2013.01); *A61K 2800/5426* (2013.01)
(58) Field of Classification Search
CPC ............... A61K 8/81; A61K 8/73; A61Q 5/06
See application file for complete search history.

(56) References Cited

U.S. PATENT DOCUMENTS

| 3,580,853 A | 5/1971 | Parran, Jr. |
| 4,638,822 A * | 1/1987 | Grollier ................. A61K 8/731 132/209 |
| 2008/0085258 A1 | 4/2008 | Nguyen et al. |

FOREIGN PATENT DOCUMENTS

| EP | 1396260 A1 | 3/2004 |
| EP | 3015135 A1 | 5/2016 |
| WO | WO-2002060399 A1 | 8/2002 |
| WO | WO-2019071194 A1 | 4/2019 |

OTHER PUBLICATIONS

"Chinese Application Serial No. 201880078908.0, Notification to Make Rectification dated Jun. 19, 2020", 1 pg.
"International Application Serial No. PCT/US2018/054706, International Preliminary Report on Patentability dated Apr. 16, 2020", 10 pgs.
"European Application Serial No. 17195272.4, Extended European Search Report dated Apr. 4, 2018", 9 pgs.
"International Application Serial No. PCT/US2018/054706, International Search Report dated Dec. 5, 2018", 6 pgs.
"International Application Serial No. PCT/US2018/054706, Written Opinion dated Dec. 5, 2018", 8 pgs.

* cited by examiner

*Primary Examiner* — Zohreh A Fay
(74) *Attorney, Agent, or Firm* — Victoria Friedman; Dennemeyer & Associates, LLC

(57) ABSTRACT

A method for treating hair comprising applying primer(s) and cationic polymer(s) onto a user's hair for improving the styling of the hair in a more manageable and reliable manner and for enhancing the stability of the final style obtained.

13 Claims, No Drawings

HAIR STYLING METHOD AND KIT THEREOF

CROSS-REFERENCE TO RELATED APPLICATION

This application is a U.S. National Stage Filing under 35 U.S.C. 371 from International Application No. PCT/US2018/054706, filed on Oct. 5, 2018, and published as WO 2019/071194 on Apr. 11, 2019, which application claims the benefit of priority to European Application Serial No. 17195272.4, filed Oct. 6, 2017, which are incorporated by reference herein in their entirety.

FIELD OF THE INVENTION

The present invention is directed to a method for treating hair comprising applying primer(s) and cationic polymer(s) onto a user's hair for improving hair styling in a more manageable and reliable manner and for enhancing the stability of the final style obtained.

BACKGROUND OF THE INVENTION

Hair styling (hair shaping) on the human scalp is probably as old as mankind itself and can be considered as an aspect of personal grooming, fashion, and cosmetics, but may also be an expression of cultural affiliation.

In principle, styling represents the crucial finish to every hair treatment as it puts the necessary final touches to every look, thereby generating the end-look of the user. While precise cuts and vibrant coloring are essential, it is the styling part that will define the final look of a user. From the stylist's perspective, a perfect finish is the signature touch for a masterpiece, and getting it right will make every customer happy. Moreover, styling is the creative part of working with hair and plays an important role in a stylist's daily business. From the user's perspective, styling represents the result of a stylist's visit or an "early morning session" in the bathroom. It is what people show to the world to express their personality, style, mood, and individualism. In other words, styling is the "playground" to express people's personality.

Different methods for styling a user's hair are known in the art. These methods generally involve wet styling, dry styling, and finishing. In principle, for wet styling, products are applied onto wet hair to create volume and touchable movement, for dry styling, products are applied on dry hair to shape and define the style of the hair while for finishing, products are applied to finish and embellish the style. Apart from the competence and the experience of the user/hairstylist, it is the choice of styling products which is critical to achieve the desired results. Styling products may generally be distinguished in products based on polymer technology, such as hairspray, gel, mousse etc., and products based on wax technology, such as creams, waxes, clay, etc.

Technically spoken, styling means to keep the single hair fibers from unwanted movement. This can be achieved by various techniques, e.g., by bridging single fibers with films or coatings, increasing friction and single fiber stiffness, and/or generating hydrophobic-hydrophobic interactions between fibers.

There is still a need for new methods for styling hair in a more manageable and reliable manner to achieve the desired end-look. Once achieved, the end-look should have a high resistance against external influences, such as moistening, or even shampooing. These methods should preferably involve the use of compositions which are less aggressive for the hair and for the scalp. Moreover, these methods should also preferably involve the use of low odour compositions.

The inventors have surprisingly found out that at least some of the before-mentioned needs may be met by the method for treating hair according to the present invention, wherein a first composition comprising one or more primer(s) is applied to a first portion of the hair to impart the surface of the hair with additional surface charges, followed by applying a second composition comprising one or more cationic polymer(s) to a second portion of the hair having at least an overlap (common area) with the first portion, followed by styling (shaping) the hair in at least part of the overlap of the hair portions.

SUMMARY OF THE INVENTION

The present invention relates to a method for treating hair comprising carrying out the following sequence of steps:
A) applying a first composition comprising one or more primer(s) to a first portion of the hair to impart the surface of the hair with additional surface charges; and
B) applying a second composition comprising one or more cationic polymer(s) to a second portion of the hair, wherein the first and second portions have at least one first common area; and
C) shaping the hair in at least part of the common area of the preceding steps.

The present invention also relates to a kit for treating hair comprising a first component comprising the first composition as defined hereinbefore, and a second component comprising the second composition as defined herein. The present invention further relates to the use of a first and second component comprising the first and second compositions as defined herein for shaping at least a portion of a user's hair.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All ratios or percentages are weight ratios or weight percentages unless specifically stated otherwise.

By "cationic polymer" it is meant any polymer comprising an overall charge at full protonation which is positive.

By "cationic coloured polymer" it is meant any cationic polymer comprising at least one chromophore and/or at least one fluorophore either in the skeleton or as pendent group.

By "cationic uncoloured polymer" it is meant any cationic polymer which does not comprise any chromophore or fluorophore either in the skeleton or as pendent group.

By "anionic polymer" it is meant any polymer comprising an overall charge at full deprotonation which is negative.

By "anionic coloured polymer" it is meant any anionic polymer comprising at least one chromophore and/or at least one fluorophore either in the skeleton or as pendent group.

By "anionic uncoloured polymer" it is meant any anionic polymer which does not comprise any chromophore or fluorophore either in the skeleton or as pendent group.

By "full protonation" it is meant the state at which the different protonable groups of a polymer are all fully protonated.

By "full deprotonation" it is meant the state at which the different deprotonable groups of a polymer are all fully deprotonated.

By "weak cationic polymer" it is meant a cationic polymer whose charge is dependent on the pH when solubilized in water.

Method for Treating Hair

The present invention relates to a method for treating hair as stated hereinbefore.

Having at least one common area between the first portion of the hair to which the first composition is applied and the second portion of the hair to which the second composition is applied ensures that at least a portion of the second composition is applied to the same portion of the hair as at least a portion of the first composition. In this portion of the hair, a primer is first applied onto hair followed by a cationic polymeric sublayer. Although not necessary, an anionic polymeric sublayer may be positioned on top of the cationic polymeric sublayer in order to finally obtain a polymer layer made of cationic and anionic polymeric sublayers. This polymeric layer is hereinafter referred to as the first polymeric layer.

Hair is naturally negatively charged. In principle, the inner sublayer of the coated hair which is positively charged can attach to the surface of the hair and the outer sublayer of the coated hair which is negatively charged can attach to the surface of the cationic polymeric sublayer positioned underneath. However, under styling aspects, it is essential that a primer is applied onto the hair prior to applying the cationic polymer sublayer for only then, the advantageous styling effects as described herein can be achieved. If present, the outer anionic sublayer of the coated hair has an electrostatic structure similar to the one of the outer layer of natural hair. It is therefore possible to apply any further hair treatment on top of the first polymeric layer that would usually be directly applied onto hair. While not wishing to be bound by theory, it is believed that by applying the primer(s) prior to the cationic polymer(s), the surface of the hair is imparted with additional surface charges at the respective pH which provide the basis for an enhanced interaction between the hair fibers and polymers placed thereon. For instance, using an oxidizing agent as primer not only lead to decolourisation of the melanin (bleaching) but also activates the hair surface such that through oxidization of proteins located at the hair surface, the overall negative charge is increased due to a removal of the F-layer of the hair. An increased overall negative charge at the respective pH of the hair surface is desirable for a better attachment of the cationic polymer applied to the hair in the subsequent step B) of the method of the present invention.

The method according to the present invention is particularly advantageous since it provides a new way for styling the hair in an easier, more manageable and reliable manner, and as such, it provides an improved styling method. The present inventors surprisingly found out that when applying the method according to present invention, washing/shampooing the hair does not necessarily destroy the final hair style as it would usually be the case for hair styles obtained by prior art styling methods. As such, the method of the present inventions ensures a more durable and more resistant hair style. Further notably is that the compositions per se which are used in the method according to the present invention are particularly advantageous since these compositions are less aggressive than known styling compositions and exhibit low odor.

Step A)

In step A) of the method according to the present invention, a first composition comprising one or more primer(s) is applied to a first portion of the hair to impart the surface of the hair with additional surface charges.

First Composition

The first composition may be applied all over the hair.

The first composition may be applied in one go or step-by-step to the hair. The first composition may be applied step-by-step, for example in case the hair is damaged. Applying the first composition step-by-step, may help to ensure that the hair is saturated with the first composition and may therefore provide a better coverage of the hair with the first composition. In a preferred aspect, the first composition may be applied to the respective hair portion in a weight ratio "first composition/hair" of 10:1 to 1:1, preferably 7:1 to 2:1, more preferably 5:1 to 3:1.

Primer(s)

The first composition comprises one or more primer(s).

The first composition may, depending on the primer(s) used, comprise a total concentration of primer(s) which is ranging from 0.1 g/L to 500 g/L, alternatively from 2 g/L to 200 g/L, alternatively from 10 g/L to 100 g/L, alternatively from 20 g/L to 80 g/L based on the total weight of the first composition. The first composition may comprise a total concentration of primer(s) ranging from 1% to 40%, preferably 5% to 40%, more preferably 10% to 35%, based on the total weight of the first composition.

The primer(s) impart the surface of the hair with additional surface charges. More specifically, the surface of the hair is imparted with additional charges specifically at the amino acid functions at the respective pH which provide the basis for an enhanced interaction between the hair fibers and the polymers placed thereon.

The primer(s) may be selected from the group consisting of cationic surfactant, anionic surfactant, amphoteric surfactant, oxidizing agent, reducing agent, pH adjusting agent, and combinations thereof.

Cationic Surfactant(s)

The first composition may comprise a total concentration of cationic surfactant(s) ranging from 1% to 15%, preferably 2% to 10%, more preferably 4% to 8%, based on the total weight of the first composition. The cationic surfactant(s) may preferably comprise one or more linear or branched group(s) comprising at least 8 carbon atoms. The cationic surfactant(s) may more preferably comprise one or more linear or branched group(s) comprising from 8 to 22 carbon atoms. The cationic surfactant(s) may even more preferably comprise one or more linear or branched group(s) comprising from 10 to 22 carbon atoms. The cationic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

The cationic surfactant(s) may be selected from the group consisting of quaternary ammonium salts, amido-amines, primary amines, secondary amines, tertiary amines and mixtures thereof.

The cationic surfactant(s) may be selected from quaternary ammonium salts having the following formula:

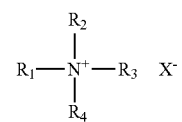

wherein:
R₁ is selected from the group consisting of linear or branched groups optionally comprising at least one heteroatom selected from oxygen, nitrogen, sulfur and halogens, wherein the linear or branched groups comprise from 6 to 22 carbon atoms, preferably from 16 to 22 carbon atoms; and R₂ is selected from the group consisting of linear or branched groups optionally comprising at least one heteroatom selected from oxygen, nitrogen, sulfur and halogens, wherein the linear or branched groups comprise from 1 to 22 carbon atoms, preferably from 16 to 22 carbon atoms, aryl groups and alkylaryl groups; and R₃ and R₄ are independently selected from the group consisting of linear or branched groups comprising from 1 to 4 carbon atoms, aryl groups and alkylaryl groups; and X⁻ is an anion selected from chloride, bromide, iodide, alkyl sulfates, phosphates, alkyl sulfonates, alkylaryl sulfonates and anions derived from organic acids or amino acids.

The linear or branched groups may be aliphatic groups. The aliphatic groups may be selected from alkyl, alkoxy and alkylamide groups.

The amino acid may be glutamic acid. The anions derived from organic acids may be acetate anions or lactates anions.

The cationic surfactant(s) may be selected from amidoamines having the following formula:

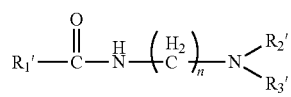

wherein:
R₁' is selected from the group consisting of linear or branched groups optionally comprising at least one heteroatom selected from oxygen, nitrogen, sulfur and halogens, wherein the linear or branched groups comprise from 10 to 22 carbon atoms, preferably from 16 to 22 carbon atoms;

R'₂ and R'₃ are independently selected from the group consisting of hydrogen, linear or branched groups optionally comprising at least one heteroatom selected from oxygen, nitrogen, sulfur and halogens, wherein the linear or branched groups comprise from 1 to 4 carbon atoms, aryl groups and alkylaryl groups;

n is integer ranging from 1 to 4.

The linear or branched groups may be aliphatic groups. The aliphatic groups may be selected from alkyl, alkoxy and alkylamide groups.

The cationic surfactant(s) may be selected from the group consisting of cetrimonium halide, stearimonium halide, behentrimonium halide, behentrimonium halide, stearamidopropyltrimonium halide, dodecyltrimethylammonium halide, didodecyldimethylammonium halide, tetradecyltrimethylammonium halide, distearyldimethylammonium halide, dicetyldimethylammonium halide, distearoylethyl dimonium halide, behenamidopropyltrimonium methosulfate, behenamidopropyl dimethylamine, stearamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, and mixtures thereof, wherein the halide is selected from bromide and chloride. The cationic surfactant(s) may preferably be selected from the group consisting of dodecyltrimethylammonium halide, didodecyldimethylammonium halide, tetradecyltrimethylammonium halide, cetrimonium halide and mixtures thereof, wherein the halide is selected from bromide and chloride.

Anionic Surfactant(s)

The first composition may comprise a total concentration of anionic surfactant(s) ranging from 1% to 15%, preferably 2% to 10%, more preferably 4% to 8%, based on the total weight of the first composition. The anionic surfactant(s) may preferably comprise one or more linear or branched group(s) comprising at least 8 carbon atoms. The anionic surfactant(s) may more preferably comprise one or more linear or branched group(s) comprising from 8 to 22 carbon atoms. The anionic surfactant(s) may even more preferably comprise one or more linear or branched group(s) comprising from 10 to 22 carbon atoms. The anionic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

Suitable anionic surfactant(s) may comprise at least one anionic functional groups at their head selected from sulfate, sulfonate, phosphate and carboxylates.

Suitable alkyl sulfates include ammonium lauryl sulfate, sodium lauryl sulfate (sodium dodecyl sulfate, SLS, or SDS), and alkyl-ether sulfates, such as sodium laureth sulfate (sodium lauryl ether sulfate or SLES), and sodium myreth sulfate.

Further suitable anionic surfactants may include Docusate (dioctyl sodium sulfosuccinate), alkyl-aryl ether phosphate, alkyl ether phosphate, alkyl carboxylate, such as sodium stearate, sodium lauroyl sarcosinate, ammonium laureth sulfate, disodium lauryl sulfosuccinate, and sodium lauryl sulphoacetate.

Preferred anionic surfactants are selected from the group consisting of sodium laurylethersulfate, sodium laurethethersulfate, sodium dodecyl sulfate, ammonium laurethethersulfat, ammonium dodecyl sulfate, alkylbenzenesulfonate, and combinations thereof.

Amphoteric Surfactant(s)

The first composition may comprise a total concentration of amphoteric surfactant(s) ranging from 1% to 15%, preferably 2% to 10%, more preferably 4% to 8%, based on the total weight of the first composition. The amphoteric surfactant(s) may preferably comprise one or more linear or branched group(s) comprising at least 8 carbon atoms. The amphoteric surfactant(s) may more preferably comprise one or more linear or branched group(s) comprising from 8 to 40 carbon atoms. The amphoteric surfactant(s) may even more preferably comprise one or more linear or branched group(s) comprising from 10 to 40 carbon atoms. The amphoteric surfactant(s) may most preferably comprise one or more linear or branched group(s) comprising from 16 to 35 carbon atoms. The linear or branched group(s) may optionally comprise at least one heteroatom selected from oxygen, nitrogen, sulfur and halogens. The linear or branched groups may be aliphatic groups.

Amphoteric (zwitterionic) surfactants have both cationic and anionic centers attached to the same molecule. The cationic part may be based on primary, secondary, tertiary amines or quaternary ammonium cations. The anionic part can be more variable and may include sulfonates, as in the sultaines CHAPS (3-[(3-Cholamidopropyl)dimethylammonio]-1-propanesulfonate) and cocamidopropyl hydroxysultaine.

Suitable amphoteric surfactants may include betaines, such as cocamidopropyl betaine, phospholipids, such as phosphatidylserine, phosphatidylethanolamine, phosphatidylcholine, and sphingomyelins.

Suitable betaines may have the following formula

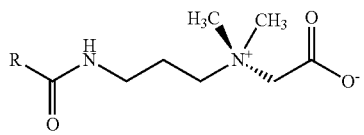

with R=alkyl chain with 5 to 21 C atoms.

Further suitable amphoteric surfactants may include sultaines which may have the following formula

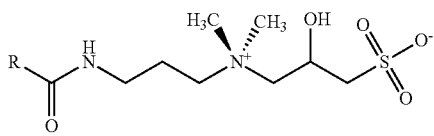

with R=alkyl chain with 5 to 21 C atoms.

Further suitable amphoteric surfactants may include taurin (2-aminoethansulfonic acid), cocoamidopropyl hydroxysultain, N-coco 3-aminopropionic acid, (or the sodium salt thereof), N-tallow 3-iminodipropionate (or the disodium salt thereof), N-carboxymethyl N-dimethyl N-9 octadecenyl ammonium hydroxide, N-cocoamidethyl N-hydroxyethylglycine, cocoamphocarboxyglycinate, cocamidopropyl betaine, and sulfobetaine.

Most preferred amphoteric surfactants are selected from the group consisting of betain, sultaines, phospholipids, aminopropionates, aminoglycinates, amphoacetate, amphodiacetate, amphopropionate, amphohydroxypropylsulfonates, and combinations thereof. Most preferred are betains selected from the group consisting of Cocamidopropyl betaine, Laurylamidopropyl betaine Tetradecyl betaine, Alkylaminopropyl betaine, Octyl betain, Cetyl betain, Staeryl betain.

Further suitable amphoteric surfactants may comprise amino acids. Specifically, amino acids with their polyampholytic character in the third composition can help to enhance the ionic and hydrophobic interactions between the hair surface. Suitable amino acids may be selected from the group consisting of alanine, arginine, asparagine, aspartic acid, cysteine, glutamic acid, glutamine, glycine, proline, selenocysteine, serine, tyrosine, histidine, isoleucine, leucine, lysine, methionine, phenylalanine, threonine, tryptophan, valine, and combinations thereof.

Oxidizing Agent(s)

The first composition may comprise a total concentration of oxidizing agent(s) ranging from 1% to 40%, preferably 5% to 40%, more preferably 10% to 35%, based on the total weight of the first composition. The oxidizing agent(s) may preferably be selected from the group consisting of hypochlorous acid, peracetic acid, persulfate, chlorine dioxide, perboric acid, salts thereof, ozone, hydrogen peroxide and mixtures thereof. The oxidizing agent(s) may more preferably be selected from the group consisting of hypochlorous acid, salts thereof and mixtures thereof. The oxidizing agent(s) may even more preferably be selected from the group consisting of sodium hypochlorite, calcium hypochlorite, potassium hypochlorite and mixtures thereof.

The first composition may comprise a total amount of oxidizing agents selected from the group consisting of sodium hypochlorite, calcium hypochlorite, potassium hypochlorite and mixtures thereof of up to 25% by total weight of the first composition. The first composition may comprise a total amount of oxidizing agents selected from the group consisting of sodium hypochlorite, calcium hypochlorite, potassium hypochlorite and mixtures thereof ranging from 0.01% to 10%, preferably from 0.2% to 2%, more preferably from 0.5% to 1.5% by total weight of the first composition. The amount of each particular oxidizing agent or mixtures thereof described hereinbefore can account for up to 100% (or 100%) of the total amount of oxidizing agents in the first composition.

The first composition of the present invention may comprise at least one oxidizing agent and/or at least one source of an oxidizing agent. The oxidizing agents may be provided in aqueous solution or as a powder which is dissolved prior to use. Preferred oxidizing agents are water-soluble peroxygen oxidizing agents. As used herein, "water-soluble" means that in standard conditions at least 0.1 g, preferably about 1 g, more preferably 10 g of the oxidizing agent can be dissolved in 1 litre of deionized water at 25° C. Suitable water-soluble oxidizing agents include, but are not limited to: inorganic peroxygen materials capable of yielding hydrogen peroxide in an aqueous solution.

According to an embodiment, the first composition may comprise a total amount of oxidizing agents ranging from 0.1% to 15%, alternatively from 0.2% to 15%, alternatively from 0.3% to 15%, alternatively ranging from 0.1% to 12%, alternatively from 0.2% to 12%, alternatively from 0.3% to 12%, alternatively from 0.1% to 7%, alternatively from 0.2% to 7%, alternatively from 0.3% to 7%0, alternatively from 1% to 7%, alternatively from 0.1% to 5%, alternatively from 0.2% to 5%, alternatively from 0.3% to 5%, alternatively from 0.5% to 5%, alternatively from 1% to 5%, alternatively from 2% to 5%, by total weight of the first composition. Alternatively, the first composition may comprise a total amount of oxidizing agents of less than 3%, alternatively less than 2%, alternatively less than 1%, alternatively less than 0.5%, alternatively less than 0.3% alternatively less than 0.1% by total weight of the first composition. The lower limit for the oxidizing agents may be at least 0.01% by total weight of the first composition. The first composition having a low amount of oxidizing agents is less damaging the hair than standard hair colouring composition which usually comprise a high concentration of oxidizing agent.

The first composition may also be substantially free of oxidizing agents, i.e. having oxidizing agents less than 0.1%, and more particularly less than 0.01% by total weight of the third composition. For example, a first composition having primer(s) such as amphoteric surfactants may be substantially free of oxidizing agents. A first composition which comprises oxidizing agent(s) as primer(s), however, may also include other primer(s), such as at least one of anionic surfactants, cationic surfactants, amphoteric surfactants, reducing agents, pH adjusting agents, and combination thereof.

Suitable water-soluble peroxygen oxidizing agents include, but are not limited to: hydrogen peroxide; inorganic alkali metal peroxides (such as sodium periodate and sodium peroxide), organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired.

The first composition may comprise a water-soluble oxidizing agent selected from the group consisting of peroxides, percarbonates (which may be used to provide a source of both oxidizing agent and carbonate ions and or ammonium ions), persulphates, and mixtures thereof. The particularly preferred oxidizing agent is hydrogen peroxide.

When the first composition of the present invention comprising oxidizing agent(s) may be obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise about 6% or about 9% of the $H_2O_2$ relative to the total weight of the developer composition. A preferred example of a developer composition with respectively about 6% and about 9% $H_2O_2$, comprises as INCI ingredients: Water, $H_2O_2$, Cetearyl Alcohol, Ceteareth-25, Salicylic Acid, Phosphoric Acid, Disodium Phosphate, Etidronic Acid. Another preferred example a developer composition comprises as INCI ingredients: Water, $H_2O_2$, cetearyl alcohol, lanolin alcohol, sodium lauryl sulfate, parfum, salicylic acid, phosphoric acid, disodium phosphate, linalool, hexyl cinnamal, etidronic acid, tocopherol. Another preferred example a developer composition comprises as INCI ingredients: Water, $H_2O_2$, cetearyl alcohol, lanolin alcohol, sodium lauryl sulfate, parfum, salicylic acid, phosphoric acid, disodium phosphate, linalool, hexyl cinnamal, etidronic acid, tocopherol.

Reducing Agent(s)

The first composition may comprise a total concentration of reducing agent(s) ranging from 1% to 40%, preferably 5% to 40%, more preferably 10% to 35%, based on the total weight of the first composition. The reducing agent(s) may be selected from the group consisting of inorganic reducing agent(s) and organic reducing agent(s), and combinations thereof.

Inorganic reducing agent(s) may preferably be selected from the group consisting of sulfide, disulfite, thiosulfate, sulfite, phosphonic acid, hydrazine, borohydride, aluminiumhydride, hydrogen, sodium sulfite, sodium bisulfite, sodium hydrogensulfite, sodiumthiosulfate, and combinations thereof.

Organic reducing agent(s) may preferably be selected from the group consisting of formic acid, ketoglutarate, DTT red, NADH/H+, dihydrolipoic acid, cysteine, vitamin C, vitamin E, Dithiothreitol (DTT), mercaptanes, thioglycolic acid, ammonium thioglycolate, sodium thioglycolate cysteine, ascorbic acid, glyceryl monothiopropionate, ammonium thiolactate, dithioerythritol, glutathione, 1,3-dithiopropanol, thioglycolamide, glyceryl monothioglycolate, glyceryl thiolactate, and combinations thereof.

The reducing agents may be provided in aqueous solution or as a powder which is dissolved prior to use. According to a particular aspect, the first composition may comprise a total amount of reducing agents ranging from 0.1% to 15%, alternatively from 0.2% to 15%0, alternatively from 0.3° % to 15%, alternatively from 0.1% to 12%, alternatively from 0.2% to 12%, alternatively from 0.3% to 12%, alternatively from 0.1% to 7%, alternatively from 0.2% to 7%, alternatively from 0.3% to 7%0, alternatively from 1% to 7%, alternatively from 0.1% to 5%, alternatively from 0.2% to 5%, alternatively from 0.3% to 5%, alternatively from 0.5% to 5%, alternatively from 1% to 5%, alternatively from 2% to 5%, by total weight of the first composition.

The first composition may include either reducing agent(s) or oxidizing agent(s).

Alternatively, the first composition may also be substantially free of reducing agents, i.e. having reducing agents less than 0.1%, and more particularly less than 0.01% by total weight of the third composition. For example, a first composition having, as primer(s), surfactants such as amphoteric surfactants may be substantially free of reducing agents. A first composition which comprises reducing agents as primer(s), however, may also include other primers, such as at least one of anionic surfactants, cationic surfactants, amphoteric surfactants, pH adjusting agents and combinations thereof.

Preferred reducing agents are thioglycolic acid, mercaptanes, ammonium thioglycolate, sodium thioglycolate cysteine, sodium sulfite, ascorbic acid, glyceryl monothiopropionate, ammonium thiolactate, dithiothreitol, dithioerythritol, glutathione, dihydrolipoic acid, 1,3-dithiopropanol, thioglycolamide, glyceryl monothioglycolate, sodium bisulfite, sodium hydrogensulfite, sodiumthiosulfate, glyceryl thiolactate, and combinations thereof.

pH Adjusting Agent(s)

The first composition may comprise a total concentration of pH adjusting agent(s) ranging from 0.01% to 10%, preferably 0.1% to 8%, more preferably 0.5% to 5%, based on the total weight of the first composition. pH adjusting agent(s) may be selected from the group consisting of ammonia, alkanolamines, guanidinium salts, alkali metal hydroxides, alkali metal carbonates, ammonium hydroxides, ammonium carbonates, inorganic acids, organic acids and mixtures thereof. The pH adjusting agents may preferably be selected from the group consisting of alkanolamines, guanidinium salts, alkali metal hydroxides, alkali metal carbonates, inorganic acids, organic acids and combinations thereof.

The alkanolamines may be selected from the group consisting of monoethanolamine, diethanolamine, triethanolamine, monopropanolamine, dipropanolamine, tripropanolamine, 2-amino-2-methyl-1-propanol, 2-amino-2-hydroxymethyl-1,3,-propandiol and combinations thereof.

The inorganic or organic acids may be selected from the group consisting of phosphoric acid, acetic acid, ascorbic acid, citric acid or tartaric acid, hydrochloric acid and combinations thereof.

By using pH adjusting agent(s) as primer, optionally in combination with any other primer described hereinbefore, the pH of the first composition can be adjusted to 8-12, preferably to 9-11. Upon applying to hair (step A)), the first composition having a pH in the before-mentioned range activates the hair surface by deprotonation of proteins located at the hair surface. As a result, the overall negative charge is increased which is desirable for a better attachment of the cationic polymer applied to the hair in the subsequent step B) of the method of the present invention.

Step B)

In step B) of the method according to the present invention, a second composition comprising one or more cationic polymer(s) is applied to a second portion of the hair.

Second Composition

The second composition may be applied all over the hair.

The second composition may be applied in one go or step-by-step to the hair. The second composition may be applied step-by-step, for example in case the hair is damaged. Applying the second composition step-by-step, may help to ensure that the hair is saturated with the second composition and may therefore provide a better coverage of the hair with the second composition.

Cationic Polymer(s)

The second composition comprises one or more cationic polymer(s).

The second composition may comprise a total concentration of cationic polymers which is ranging from 0.1 g/L to 100 g/L, alternatively from 0.5 g/L to 100 g/L, alternatively from 2 g/L to 50 g/L, alternatively from 5 g/L to 10 g/L.

The cationic polymer(s) may be coloured.

The cationic polymer(s) may preferably be uncoloured.

The cationic polymer(s) may comprise one or more amino functional group(s) per polymer chain, wherein the amino functional group(s) are selected from the group consisting of primary, secondary, tertiary, quaternary amino functional groups and mixtures thereof, preferably from the group consisting of secondary, tertiary, quaternary amino functional groups and mixtures thereof, more preferably from quaternary amino functional groups.

The cationic polymer(s) may be selected from the group consisting of polyethyleneimine, polyallylamine hydrochloride, polydiallyldimethylammonium chloride, polyvinylamine, copolymers thereof and mixtures thereof. The cationic polymer(s) may preferably be selected from the group consisting of polyethyleneimine, polydiallyldimethylammonium chloride, copolymers thereof and mixtures thereof.

The copolymers may be random or block copolymers.

The cationic polymer(s) may be linear or branched.

The cationic polymer(s) may be selected from the group consisting of:

a) Linear polyethyleneimine of the formula:

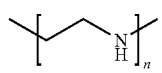

in which n is an integer representing the degree of polymerization, wherein n ranges from 50 to 20,000, alternatively from 100 to 3,500;

b) Branched polyethyleneimine consisting of primary, secondary and tertiary amine groups of the formula:

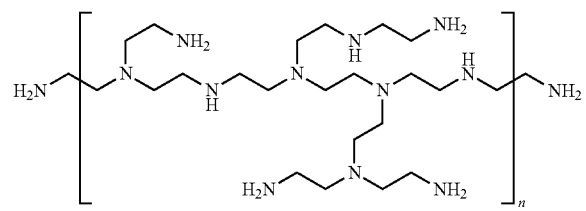

in which n is an integer representing the degree of polymerization, wherein n ranges from 5 to 4,000, alternatively from 50 to 500;

c) Polyallylamine hydrochloride of the formula:

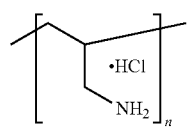

in which n is an integer representing the degree of polymerization, wherein n ranges from 50 to 20,000, alternatively from 150 to 2000;

d) Polydiallyldimethylammonium chloride of the formula:

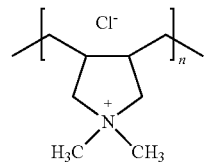

in which n is an integer representing the degree of polymerization, wherein n ranges from 10 to 20,000, alternatively from 150 to 4,000;

copolymers thereof and mixtures thereof.

The copolymers may be random or block copolymers.

The cationic polymer(s) may have a charge density at full protonation of at least 0.3, preferably at least 0.6, more preferably at least 0.8, even more preferably at least 1.0 positive charges per monomer unit.

The cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

First and Second Compositions

The first and the second portions of the hair may be the same, or may at least have an overlap. An overlap between two or more hair portions is generally referred herein as "common area" ("common region"). As such, the first and the second portions of the hair may have at least a "first common area" ("first common region"). The first and the second compositions may be applied all over the hair. Step B) is carried out after step A). Step B) may be carried out immediately after step A) or at least 1 hour after step A) or at least 24 hours after step A) or at least 10 days after step A) or at least one month after step A).

Step C)

In step C) of the method according to the present invention, the hair is shaped in at least part of the common area of the preceding steps. In principle, this means that shaping is carried out in those hair areas (hair regions) which have been treated with both the first composition and the second composition according to steps A) and B) as defined herein. In other words, shaping is carried out in at least part of the first common area. In the event that an additional step is carried out before step C), shaping is carried out in those hair areas (hair regions) which were subject to at least one of, and preferably to all of the prior treatment steps.

Shaping (Styling)

Shaping (styling) hair comprises rearranging the hair to impart a given shape (style) to the hair. By "shaping" it is meant any method applied to a first portion of a hair having a first initial shape that imparts the first portion of the hair with a second shape different to the first shape, at least temporarily, for at least 1 hour, particularly for at least two hours, more particularly for at least 4 hours, even more particularly for at least 8 hours, without requiring any further auxiliary means for maintaining the second shape. For carrying out shaping, products and tools can be used to create new shape, style, volume and texture as well as to maintain the created look (hold). Shaping is selected from the group consisting of straightening, spiking, curling, fixating, helping braiding as well as refreshing/touching-up, creating volume, creating texture, and combinations thereof. Shaping does preferably not include colouring, rinsing, shampooing, conditioning and/or drying the hair.

Step C) is carried out after step B). Step C) may be carried out immediately after step B) or at least 1 hour after step B) or at least 24 hours after step B) or at least 10 days after step B) or at least one month after step B).

Step D)

The method according to the present invention my further comprise D) applying a third composition comprising one or more anionic polymer(s) to a third portion of the hair.

Third Composition

The third composition may be applied all over the hair.

The third composition is applied after the second composition to the hair.

The third composition may be applied in one go or step-by-step to the hair. The third composition may be applied step-by-step, for example in case the hair is damaged. Applying the third composition step-by-step, may help to ensure that the hair is saturated with the third composition and may therefore provide a better coverage of the hair with the third composition.

Anionic Polymer(s)

The third composition comprises one or more anionic polymer(s).

The third composition may comprise a total concentration of anionic polymers which is ranging from 0.1 g/L to 100 g/L, alternatively from 0.5 g/L to 100 g/L, alternatively from 2 g/L to 50 g/L, alternatively from 5 g/L to 10 g/L.

The anionic polymer(s) may be coloured.

The anionic polymer(s) may preferably be uncoloured.

The anionic polymer(s) may comprise one or more functional group(s) per polymer chain selected from the group consisting of phenyl group, alkyl groups comprising at least 8 carbon atoms and mixtures thereof.

The anionic polymer(s) may be selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The anionic polymer(s) may preferably be selected from the group consisting of polystyrene sulfonate salts, polystyrene sulfonate/polystyrene copolymer salts, copolymers thereof and mixtures thereof.

The copolymers may be random or block copolymers.

The anionic polymer(s) may be linear or branched.

The anionic polymers may be selected from the group consisting of:

a) Polystyrene sulfonate (PSS) sodium salt of the formula:

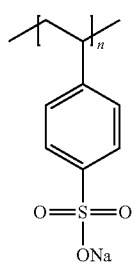

in which n is an integer representing the degree of polymerization, wherein n ranges from 50 to 20,000, alternatively from 150 to 2500;

b) Co-polymer of polystyrene sulfonate (PSS) sodium salt and poly(4-styrenesulfonic acid-co-maleic acid) of the formula:

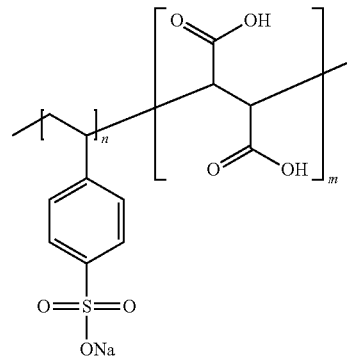

in which n and m are integers representing the degree of polymerization, wherein n+m ranges from 50 to 20,000, alternatively from 150 to 2500;

c) λ-Carrageenan;

d) Dextran sulfate sodium salt;

e) Polyacrylic acid (PAA) of the formula:

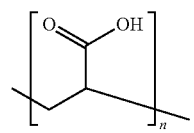

in which n is an integer representing the degree of polymerization, wherein n ranges from 50 to 20,000, alternatively from 150 to 1,000;

f) Alginic acid sodium salt;

g) Carboxymethylcellulose sodium salt of the formula:

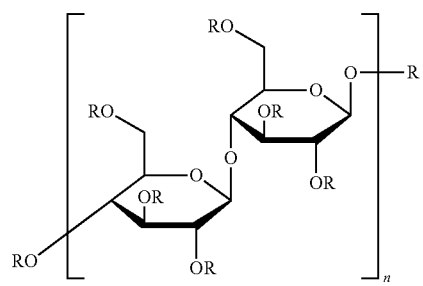

in which:

R is H or $(CH_2)_2COONa$ and n is an integer representing the degree of polymerization; copolymers thereof and mixtures thereof.

The copolymers may be random or block copolymers.

The anionic polymer(s) may have a charge density at full deprotonation of at least 0.3, alternatively at least 0.6, alternatively at least 0.8, alternatively at least 1.0 negative charges per monomer unit.

The anionic polymer(s) may have a weight average molecular weight of at least 1 kD, alternatively from 10 kD to 1000 kD, alternatively from 70 to 500 kD.

First, Second and Third Compositions

The third composition may be applied to a third portion of the hair. The third portion of the hair may be the same as the first portion and/or the second portion of the hair, or may at least have an overlap, referred herein as "common area" ("common region"), with the first and the second portions of the hair. As such, the third portion of the hair may have at least one "second common area" ("second common region") with the "first common area" ("first common region"). The third composition may be applied all over the hair. Step D) may be carried out between steps B) and C). Step D) may be carried out immediately after step B) or at least 1 hour after step B) or at least 24 hours after step B) or at least 10 days after step B) or at least one month after step B). On the other hand, step D) may be carried out immediately prior to step C), or at least 1 hour prior to step C), or at least 24 hours prior to step C), or at least 10 days prior to step C), or at least one month prior to step C).

Repeating Steps

In the event that step D) is carried out, the method may further comprise, after step D) and prior to step C), repeating steps B) and D) at least once. Preferably, steps B and D) may be repeated once, twice, three times or four times. Repeating steps B) and D) ensures that at least one additional polymeric layer made of an anionic polymeric sublayer and a cationic polymeric sublayer is positioned on top of the first polymer layer made of the cationic polymer(s) of the second composition and the anionic polymer(s) of the third composition.

In the event that step D) is carried out, the method may further comprise after step D) (and preferably after each of the repeated steps D)), and prior to step C), repeating step B) once. Repeating step B) once ensures that the uppermost surface of the treated hair portion is formed by a cationic polymeric sublayer, and as such, that the uppermost surface of the treated hair portion is positively charged.

Additional Steps

Removal of the Excess of the Compositions

At least one of steps A), B), C) and D), preferably all the steps A), B), C) and D) may further comprise the subsequent sub-step of removing the excess of the respective composition(s) with fingers and/or a towel.

Application of Energy

Steps A), B), C), and/or D) may further comprise the subsequent sub-step of applying energy to the hair in the form of heat, ultrasounds, infrared and/or microwaves. This sub-step may be carried out either after the application of the first, second, or, if applied, after the third composition to the hair or after removing the excess of the first, second and/or third composition from the hair. While not wishing to be bound by theory, it is believed that applying energy to the hair may stabilize the deposition of the respective compounds (e.g., the cationic polymer) on the hair. The hair may be heated to a temperature ranging from 5° C. to 70° C., alternatively 20° C. to 60° C., alternatively 40° C. to 60° C.

Washing and/or Rinsing

The method according to the present invention may further comprise prior to step A), or after steps A), B), C), or D) applying a fourth composition to a fourth portion of the hair for washing and/or rinsing the hair. The fourth composition may comprise a liquid selected from the group consisting of a cosmetically acceptable solvent (preferably water), a solution comprising a cosmetically acceptable solvent and a cosmetically acceptable salt, a shampoo composition and mixtures thereof.

The fourth composition may be applied to a fourth portion of the hair. The fourth portion of the hair may be the same as the first portion and/or the second portion and/or the third portion of the hair, or may at least have an overlap ("common area"/"common region"), with the first, the second and the third portion of the hair. The fourth portion of the hair may have at least one "third common area" ("second common region") with the "first common area" ("first common region") or with the "second common area" ("second common region"). The fourth composition may be applied all over the hair. The fourth composition may be applied immediately prior to step A), or immediately after steps A), B), C) or D). The fourth composition may be applied at least 1 hour prior to step A), or at least 1 hour after steps A), B), C) or D), or at least 24 hours prior to step A), or at least 24 hours after steps A), B), C) or D), or at least 10 days prior to step A), or at least 10 days after steps A), B), C) or D), or at least one month prior to step A), or at least one month after steps A), B), C) or D).

Pre-Treatment

The hair may further be pretreated prior to step A) to additionally modify the number of positive or negative charges in some portions of the hair or all over the hair. This pretreatment may be done using means such as plasma treatment, ozone treatment, electrowetting, dry or wet ion-treatment.

Hair Colouring Step

The method according to the present invention may further comprise prior to step A), and preferably after washing and/or rinsing as defined herein, a step of colouring the hair by applying a fifth composition. The fifth composition may comprise color pigment(s) and/or oxidative dye precursor(s) and/or direct dyes.

The step of colouring the hair may comprise applying one or more pigment(s) and/or one or more direct dyes and/or one or more oxidative dye precursor(s) to a fifth portion of the hair, wherein the fifth portion of the hair has at least one common area with the first, second, or third common areas (common regions).

Having at least one common area (common region) between the fifth portion of the hair to which the fifth composition is applied and the first, second or third common area (common region) defined hereinbefore ensures that the fifth composition is applied to the same portion of the hair that had already been treated with the first, the second, and optionally the third and fourth compositions.

The hair colouring step may be carried out immediately prior to step A), or at least 1 hour prior to step A), or at least 24 hours prior to step A), or at least 10 days prior to step A), or at least one month prior to step A). On the other hand, the hair colouring step may be carried out after applying the before-mentioned fourth composition. The hair colouring step may be carried out immediately after applying the before-mentioned fourth composition, or at least 24 hours after applying the before-mentioned fourth composition, or at least 10 days after applying the before-mentioned fourth composition, or at least one month after applying the before-mentioned fourth composition.

Fifth Composition

Pigment(s)

As described hereinbefore, the fifth composition may comprise one or more pigment(s). The pigments may be coloured pigments which impart colour effects to the hair (keratin fibres), or they may be lustre effect pigments which impart desirable and aesthetically pleasing lustre effects to the hair (keratin fibres).

The fifth composition may comprise pigments having a $D_{50}$ particle diameter of from 1 nm to 60 micron. Particle diameter is represented by $D_{50}$, which is the median diameter by volume. $D_{50}$ is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.02 micron to 2000 micron. $D_{50}$ is expressed as $x_{50}$ in ISO 13320:2009(en). Laser diffraction measures particle size distributions by measuring the angular variation in intensity of light scattered as a laser beam passes through a dispersed particulate sample analyser and the particle size is reported as a volume equivalent sphere diameter. A discussion of calculating $D_{50}$ is provided in Barber et al, Pharmaceutical Development and Technology, 3(2), 153-161 (1998), which is incorporated herein by reference.

The fifth composition may comprise pigments having a $D_{50}$ particle diameter of from 100 nm to 20 micron. The pigments may be present in the composition in undissolved form. The fifth composition may comprise a total amount of pigments ranging from 0.01% to 25%, or from 0.1% to 20%, or from 1% to 15%, or from 4% to 10% pigment by total weight of the composition. The pigments are colorants which are virtually insoluble in the composition, and may be inorganic or organic. Inorganic-organic mixed pigments are also possible. The fifth composition may comprise inorganic pigments. The advantage of inorganic pigments is their excellent resistance to light, weather and temperature. The inorganic pigments may be of natural origin, and are, for example, derived from material selected from the group consisting of chalk, ochre, umber, green earth, burnt sienna, and graphite. The pigments may be white pigments, such as, for example, titanium dioxide or zinc oxide, or are black pigments, such as, for example, iron oxide black, or are coloured pigments, such as, for example, ultramarine or iron oxide red, lustre pigments, metal effect pigments, pearlescent pigments, and fluorescent or phosphorescent pigments. Alternatively, the pigments may be coloured, non-white pigments. The pigments may be selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments). The pigments may be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), and mixtures thereof.

The pigments may be pearlescent and coloured pigments based on mica which are coated with a metal oxide or a metal oxychloride, such as titanium dioxide or bismuth oxychloride, and optionally further colour-imparting substances, such as iron oxides, Prussian blue, ultramarine, and carmine. The colour exhibited by the pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for colour travel pigments that display colour shifting effects depending on the viewing angle and are based on either natural mica, $SiO_2$ or calcium aluminium borosilicate flakes, coated with varying layers of $TiO_2$. Pigments from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and $TiO_2$) having a $D_{50}$ particle diameter of 5 to 25 micron and also KTZ® CELESTIAL LUSTER (mica and $TiO_2$, 10 to 60 micron) as well as KTZ® CLASSIC WHITE (mica and $TiO_2$, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection colour and is composed of platelets of synthetic fluorphlogopite and coated with titanium dioxide and iron oxides. Also useful is Duocrome® RV 524C from BASF, which provides a two colour look via a lustrous red powder with a violet reflection powder due to its composition of mica, titanium dioxide and carmine.

The pigments may be organic pigments. The organic pigments may be selected from the group consisting of natural pigments sepia, gamboge, bone charcoal, Cassel brown, indigo, chlorophyll and other plant pigments. The synthetic organic pigments may be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof.

The pigments may be selected from the group consisting of iron oxide, titanium dioxide, mica, borosilicate, and combinations thereof. The pigments may comprise an iron oxide ($Fe_2O_3$) pigment. The pigment may comprise a combination of mica and titanium dioxide.

Oxidative Dye Precursor(s)

The fifth composition may comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the fifth composition may comprise a total amount of oxidative dye precursors ranging up to 12%, preferably from 0.1% to 10%, more preferably from 0.3% to 8%, even more preferably from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenyl amino) ethyl azanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy] ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene- 1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methyl phenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)propane, 2,2'-(2-methyl-1,3-phenylene)bis(azanediyl) diethanol, benzene-1,3-diamine, 2,2'-(4,6-diamino-1,3-phenyl ene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions of the invention are obtained by mixing a tint composition and a developer composition, the primary intermediates and couplers are usually incorporated into the tint composition.

Direct Dye(s)

The fifth composition may comprise direct dye(s), in an amount sufficient to provide colouring, particularly with regard to intensity. Typically, the fifth composition may comprise a total amount of direct dye(s) ranging from about 0.05% to about 4%, by total weight of the fifth composition.

Suitable direct dyes include but are not limited to: Acid dyes such as Acid Yellow 1, Acid Orange 3, Acid Black 1. Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenyl hydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the fifth composition is obtained by mixing a tint composition and a developer composition, the direct dyes are usually incorporated into the tint composition.

Cationic Coloured Polymers and Anionic Coloured Polymers

As defined above, the cationic polymer(s) and/or the anionic polymer(s) used in steps B) and D) may be coloured.

The cationic coloured polymers and the anionic coloured polymers used in the present invention comprise at least one chromophore and/or at least one fluorophore. Any of the hereinbefore exemplified cationic polymers or anionic polymers can comprise at least one chromophore and/or at least one fluorophore either in the skeleton or as pendent group.

The chromophores may be selected from the group consisting of nitrobenzene, azo, imine, hydrazine, phenothiazine, xanthene, phenanthridine, phthalocyanin and triarylmethane-based dyes, derivatives thereof, derivatives obtained from direct dyes containing a carbonyl group and mixtures thereof. The chromophores may be selected from the group consisting of acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, derivatives thereof and mixtures thereof.

The chromophores may be substituted with at least one amine, hydroxyl, sulfate, sulfonate, carboxylate, phosphate, phosphonate, or halide group. These chromophores may be selected from the group consisting of derivatives of acidic nitro direct dyes, acidic azo dyes, acidic azine dyes, acidic triarylmethane dyes, acidic indoamine dyes and non-quinone acidic natural dyes, and mixtures thereof.

The chromophores may also be selected from derivatives of any of the direct dyes exemplified in the direct dyes section of this application.

The fluorophores may be selected from the group consisting of derivatives from di-, tetra- or hexa-sulfonated triazine-stilbenes, coumarins, imidazolines, diazoles, triazoles, benzoxazolines, biphenyl-stilbenes optical brighteners, and mixtures thereof.

A cationic coloured polymer or an anionic coloured polymer may comprise the same type of chromophore and/or fluorophore or different types of chromophores and/or fluorophores. Having a cationic coloured polymer or an anionic coloured polymer with different types of chromophores and/or fluorophores may help to cover a broad range of colour shades which can be obtained on hair which are coloured according to the method of the present wherein the first composition or the second composition comprises such a cationic coloured polymer or such an anionic coloured polymer.

The cationic coloured polymers may be selected from the group consisting of:

i. Coloured linear or branched polyethyleneimine (PEI) of the formula:

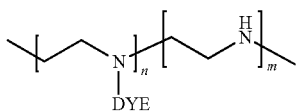

in which n and m are integers representing the degree of polymerization, wherein m/n ranges from 0 to 1,000 provided that n is different from 0 and/or m+n ranges from 50 to 20,000, alternatively from 100 to 3,500;

ii. Coloured polyallylamine of the formula:

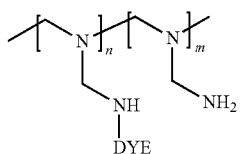

in which n and m are integers representing the degree of polymerization, wherein m/n ranges from 0 to 1,000 provided that n is different from 0 and/or m+n ranges from 50 to 20,000, alternatively from 150 to 2000;

iii. Coloured polydiallyldimethylammonium chloride of the formula:

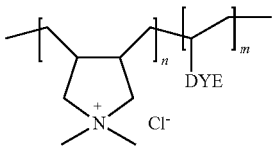

in which n and m are integers representing the degree of polymerization, wherein m/n ranges from 0 to 1,000 provided that n is different from 0 and/or m+n ranges from 10 to 20,000, alternatively from 100 to 4000;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The cationic coloured polymers may be selected from linear polyethyleneimine (PEI)—Rhodamine B of the formula:

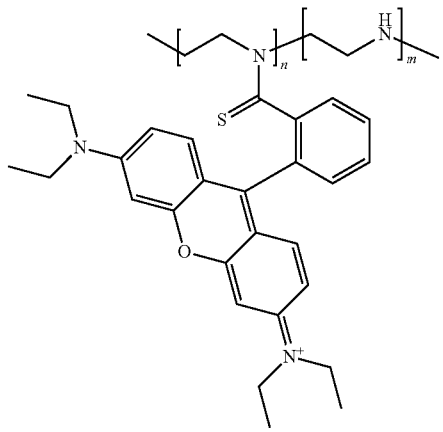

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

The anionic coloured polymers may be selected from anionic coloured polymers with the following formula:

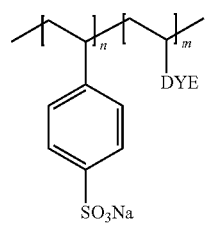

in which n and m are integers representing the degree of polymerization, wherein m/n may range from 0 to 1,000 provided that n is different from 0 and/or m+n may range from 50 to 20,000, alternatively from 150 to 500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

First to Fifth Compositions

Solvents

The first to fifth compositions which are used to carry out the method according the present invention may further comprise at least one solvent. The solvent may be selected from water, or a mixture of water and at least one organic solvent to dissolve the compounds that would not typically be sufficiently soluble in water. The first to fifth compositions may be aqueous solutions.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, the compositions may comprise water as a main ingredient, particularly in a total amount ranging from at least 50%, alternatively from at least 60%, alternatively from at least 70%, by total weight of the composition. Typically, when present, the compositions comprise a total amount of organic solvents ranging from about 1% to about 30%, by total weight of the composition.

Salt

The first to fifth compositions may comprise at least one cosmetically acceptable salt at a concentration ranging from 0 to 1.5 mol/L, preferably from 0.05 to 1 mol/L, more preferably from 0.2 to 0.5 mol/L.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. The cosmetically acceptable salt may be sodium chloride.

Applicators

The first to fifth compositions may be applied to the hair using an applicator such as a brush or a sponge. Alternatively, the first to fifth composition may be applied to the hair by spraying or foaming the first to fifth composition to the hair or by dipping the hair into the first to fifth composition. Alternatively, the first to fifth composition may be applied to the hair using printing technology.

Other Ingredients

The first to fifth compositions according to the present invention may comprise, in addition to the ingredients indicated above, further ingredients in order to further enhance the properties of the composition, as long as these are not excluded by the claims.

Suitable further ingredients include, but not limited to: alkalizing agents; oxidative dye precursors, direct dyes; chelants; radical scavengers; pH modifiers and buffering agents; thickeners and/or rheology modifiers; carbonate ion sources; peroxymonocarbonate ion sources; surfactants; polymers; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Alkalizing Agents

The first to fifth compositions according to the present invention may further comprise at least one alkalizing agent. Any alkalizing agent known in the art may be used.

Typically, the first to fifth compositions may comprise a total amount of alkalizing agents ranging from 0.1% to 10%, alternatively from 0.5% to 6%, alternatively from 1% to 4%, by total weight of the composition.

Alternatively, the first to fifth compositions may comprise a total amount of alkalizing agents of less than 1%, preferably less than 0.5%, more preferably less than 0.3%, even more preferably less than 0.1% by total weight of the composition. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The first to fifth compositions may comprise a total amount of ammonia of less than 1%, preferably less than 0.5%, more preferably less than 0.3%, even more preferably less than 0.1% by total weight of the composition. The first to fifth compositions may most preferably be free of ammonia. These embodiments are particularly interesting since such compositions are low odour compositions.

Preferably, if present, the ammonium ions and carbonate ions are present in the composition at a weight ratio of from 3:1 to 1:10, alternatively from 2:1 to 1:5.

When the compositions of the present invention is obtained by mixing a developer and a tint composition prior to use, the alkalizing agent is generally present in the tint composition.

Oxidative Dye Precursors

The second to fourth compositions according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the second to fourth compositions may comprise a total amount of oxidative dye precursors ranging up to 12%, preferably from 0.1% to 10%, more preferably from 0.3% to 8%, even more preferably from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1 (5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene- 1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methyl naphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions of the invention are obtained by mixing a tint composition and a developer composition, the primary intermediates and couplers are usually incorporated into the tint composition.

Chelants

The first to fifth compositions according to the present invention may further comprise at least one chelant (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the first to fifth compositions may comprise a total amount of chelants ranging from at least 0.01%, preferably from 0.01% to 5%, more preferably from 0.25% to 3%, even more preferably from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—PO$_3$H$_2$) or its derivative—PO$_3$R$_2$, wherein R$_2$ is a C$_1$ to C$_6$ alkyl or aryl group and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diaminetetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the first to fifth compositions may comprise a chelant selected from the group consisting of diethylenetriamine-N,N',N"'-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the compositions of the invention are obtained by mixing a tint composition and a developer composition, the chelants may be incorporated in the tint composition and/or in the developer composition. A chelant is usually present in the developer composition for stability reason.

Radical Scavengers

The first to fifth compositions according to the present invention may further comprise at least one radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during a colouring/bleaching process.

Typically, the first to fifth compositions may comprise a total amount of radical scavengers ranging from 0.1% to 10%, preferably from 1% by weight to 7%, by total weight of the composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, I-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

The second to fifth compositions according to the present invention may further comprise, in addition to the alkalizing agent discussed above, a pH modifier and/or buffering agent.

Suitable pH modifiers and/or buffering agents include, but are not limited to: ammonia; alkanolamines (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The first to fifth compositions according to the invention may further comprise at least one thickener in an amount sufficient to provide the compositions with a viscosity so that it can be readily applied to the hair without unduly dripping off the hair and causing mess.

Typically, the first to fifth compositions may comprise a total amount of thickeners ranging from at least 0.1%, preferably at least 0.5%, more preferably at least 1%, by total weight of the composition.

Suitable thickeners include, but are not limited to: associative polymers, polysaccharides, non-associative polycarboxylic polymers, and mixtures thereof.

Carbonate Ion Sources

The first to fifth compositions according to the present invention may further comprise at least one source of carbonate ions, carbamate ions, hydrogen carbonate ions, and mixtures thereof in a sufficient amount to reduce damage to the hair during the optional colouring process.

Typically, the first to fifth compositions may comprise a total amount of a carbonate ion source ranging from 0.1% to 15%, preferably from 0.1% to 10%, more preferably from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The first to fifth compositions according to the present invention may further comprise at least one conditioning agent, and/or be used in combination with a composition comprising at least one conditioning agent.

Typically, the first to fifth compositions may comprise a total amount of conditioning agents ranging from 0.05% to 20%, preferably from 0.1% to 15%, more preferably from 0.2% to 10%, even more preferably from 0.2% to 2%, most preferably from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Surfactant(s)

The second to fifth compositions according to the present invention may further comprise one or more surfactant(s).

Typically, the second to fifth compositions may comprise a total amount of surfactants ranging from 0.1% to 30%, preferably from 2% to 30°/%, more preferably from 8% to 25%, even more preferably from 10% to 20%, by total weight of the composition.

The second to fifth compositions may comprise one or more surfactant(s) selected from the group consisting of anionic surfactants, amphoteric surfactants, nonionic surfactants and mixtures thereof. The second to fifth compositions may comprise a total amount of anionic surfactants ranging from 0.10% to 20%, preferably from 0.1% to 15%, more preferably from 5% to 15%, by total weight of the compositions; and a total amount of amphoteric and/or nonionic components, which may range independently from each other from 0.1% to 15%, preferably from 0.5% to 10%, more preferably from 1% to 8%, by total weight of the compositions.

Ionic Strength

The first to fifth compositions of the present invention may further have an ionic strength as defined herein of less than 1.35 mole/kg, preferably from 0.10 to 0.75 mole/kg, more preferably from 0.20 to 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the compositions is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: $I=½((2×(+1)^2×0.050)+(+1)^2×0.020+(-2)^2×0.050+(-1)^2×0.020)=0.17$ M.

Foam

The first to fifth compositions of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides; polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Hair Colouring Kit

The present invention also relates to a kit for treating hair comprising a first component comprising the first composition as defined hereinbefore, a second component comprising the second composition as defined hereinbefore, and optionally further comprising at least one of:

a third component comprising the third composition as defined hereinbefore, a fourth component comprising the fourth composition as defined hereinbefore, a fifth component comprising the fifth composition as defined hereinbefore.

Use

The present invention further relates to the use of a first and second component comprising the first and second compositions as defined hereinbefore for shaping of at least a portion of a user's hair.

EXAMPLES

The following are non-limiting examples of the method of the present invention. The examples are given solely for the purpose of illustration and are not to be construed as limitations of the present invention, as many variations thereof are possible without departing from the spirit and scope of the invention, which would be recognized by one of ordinary skill in the art.

Study Design

The objective of this study was to characterize the styling effect and styling resistance under controlled conditions.

12 clients were recruited in Germany (up to shoulder length hair—fine/coarse/grey) and the effect of primer+cationic polymer (e.g., PEI) on styling as well as the washing resistance of the styling obtained was studied over time. The assessment was performed by stylists as well as by clients via diary at the following stages:

direct effect,
after 3 washes,
after 8 washes,
after 15 washes.

Clients received Wella Brilliance shampoo to be used at home. They also received Wella Brilliance conditioner for eventual usage.

Application Procedure (Half Head)

The method was performed half-head and off-scalp.

| LBL - Style | LBL - Style | LBL - Style two PEI, one DxS | LBL - Style |
|---|---|---|---|
| Primer + PEI | One double layer | layer | Two double layers |
| 3 models | 3 models | 3 models | 3 models |
| Fine blond hair, | Fine blond hair, | Fine blond hair, | Fine blond hair, |
| Grey hair difficult to style, | Grey hair difficult to style, | Grey hair difficult to style, | Grey hair difficult to style, |
| Frizzy hair | Frizzy hair | Frizzy hair | Frizzy hair |
| Application procedure | Application procedure | Application procedure | Application procedure |
| Shampoo (Non-conditioning) | Shampoo (Non-conditioning) | Shampoo (Non-conditioning) | Shampoo (Non-conditioning) |
| Primer | Primer | Primer | Primer |
| PEI Layer | PEI Layer | PEI Layer | PEI Layer |
|  | DxS Layer | DxS Layer | DxS Layer |
|  |  | PEI Layer | PEI Layer |
|  |  |  | DxS Layer |
| Rinse | Rinse | Rinse | Rinse |
| Assessment wet | Assessment wet | Assessment wet | Assessment wet |
| Shampoo with Brilliance | Shampoo with Brilliance | Shampoo with Brilliance | Shampoo with Brilliance |
| Assessment wet | Assessment wet | Assessment wet | Assessment wet |
| Dry & Style | Dry & Style | Dry & Style | Dry & Style |
| Assessment dry | Assessment dry | Assessment dry | Assessment dry |
| Follow-up after 3 8 and 15 washes | Follow-up after 3, 8 and 15 washes | Follow-up after 3, 8 and 15 washes | Follow-up after 3, 8 and 15 washes |
| Shampoo with Brilliance | Shampoo with Brilliance | Shampoo with Brilliance | Shampoo with Brilliance |
| Assessment wet | Assessment wet | Assessment wet | Assessment wet |
| Assessment dry | Assessment dry | Assessment dry | Assessment dry |

Application Details
1. Shampoo step before color application:
The shampoo was used to remove remains of silicon or styling products and was used as normal hair shampoo. One washing step was performed with non-conditioning shampoo before LBL application to remove depositions on hair.
Application amount: 0.1 g shampoo per gram hair. The total shampoo was removed with water from the hair.
2. Primer Solution:
The Primer Solution was used as leave in. Application amount 2 ml per gram hair.
Residence time: 1 min at room temperature.
Excess solution was wiped off with a tissue.
3. PEI-Layer:
Application amount: max. of 4 g solution per gram hair (max. amount half head is 50 g) Residence time: 15 min under the climazon—Color setting (no foil wrapping). After residence time, it was rinsed over with water.
4. Optional DxS-Layer (Sealing-Layer):
Application amount: max. of 4 g solution per gram hair
Residence time: 5 min at room temperature.
5. Optional repeating steps 3 and/or 4 once or twice.
6. Final Shampoo wash
After application of the ON Layers the full head was washed with WELLA PROFESSIONAL BRILLIANCE Shampoo for fine hair.
Assessment Details & Criteria
Stylist assessed hair at stages defined above. Assessment Criteria:
Manageability (including stability)
Care
Frizz
Density
Clients received a diary to record the washing frequency as well as a questionnaire capturing observations regarding feel (wet & dry) as well as manageability, combing, style retention, shine, volume, care effect, thickness.
Results
Stylist Assessment & Observations
Overall, the application of primer+cationic polymer (by carrying out steps A) and B) of the method according to the present invention) was a feasible way for styling hair in a manageable and reliable manner. Hair was easier to create a desired style when drying with the hair dryer. In some cases this also led to less frizz and smoother hair feel due to reduction in frizz especially at the ends of hair.
The effect was strongest after first application and with damaged hair, but also still apparent with least damaged/uncoloured grey hair.
Best styling was achieved when applying 1.5 layers (i.e. two PEI, one DxS) and ending with a PEI layer. The hair feel improved significantly in wet condition and styling effect was still present. The worst styling results were achieved when applying 2 double layers. Still, also 2 double layers provided a satisfactory styling quality as compared to conventional styling methods. Notably, almost all of the final hair styles (10 out of 12) obtained by the method as described hereinbefore survived not less than 8 washes with shampoo while 6 out of 12 final hair styles obtained by the method as described hereinbefore even survived 15 washes with shampoo.
Client Observations
9 out of 12 clients observed positive effects on their hair (easier to style, less frizz, better form definition).
The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A method for styling hair comprising carrying out the following sequence of steps:
   A) applying a first composition comprising one or more primers to a first portion of the hair to impart a surface of the hair with additional surface charges;
   B) applying a second composition comprising one or more cationic polymers to a second portion of the hair, wherein the first portion and the second portion have at least one first common area; and
   C) shaping the hair in at least part of the first common area.

2. The method according to claim 1, further comprising between steps B) and C):
   D) applying a third composition comprising one or more anionic polymers to a third portion of the hair, wherein the third portion has at least one second common area with the first common area.

3. The method according to claim 2, further comprising: repeating steps B) and D).

4. The method according to claim 2, further comprising: repeating step B).

5. The method according to claim 1, further comprising prior to step A), or after steps A), B), C) or D):
   applying a fourth composition to a fourth portion of the hair for at least one of washing or rinsing the hair, the fourth composition comprising a liquid selected from the group consisting of a cosmetically acceptable solvent, a solution comprising a cosmetically acceptable solvent and a cosmetically acceptable salt, a shampoo composition, and mixtures thereof,
   wherein the fourth portion has at least one third common area with the first common area or the second common area.

6. The method according to claim 1, wherein shaping comprises rearranging the hair to impart a given shape to the hair.

7. The method according to claim 1, wherein step C) comprises straightening, spiking, curling, fixating, braiding, refreshing, touching-up, creating volume, creating texture, and combinations thereof.

8. The method according to claim 1, wherein the one or more primers are selected from the group consisting of a cationic surfactant, an anionic surfactant, an amphoteric surfactant, an oxidizing agent, a reducing agent, a pH adjusting agent, and combinations thereof.

9. The method according to claim 1, wherein at least one of the one or more cationic polymers or the one or more anionic polymers are uncolored, and wherein optionally no colored anionic or colored cationic polymer is applied to the hair after step A).

10. The method according to claim 1, wherein the one or more cationic polymers are selected from the group consisting of polyethyleneimine, polyallylamine hydrochloride, polyvinylamine, copolymers thereof, and mixtures thereof.

11. The method according to claim 2, wherein the one or more anionic polymers comprise one or more monomer units comprising one or more functional groups selected from the group consisting of sulfate, sulfonate, carboxylate, phosphate, phosphonate groups, and mixtures thereof.

12. The method according to claim 11, wherein the one or more anionic polymers are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof, and mixtures thereof.

13. The method according to claim 1, wherein at least one of:
- the first composition comprises a total concentration of primers ranging from 0.1 g/L to 500 g/L; or
- the second composition comprises a total concentration of cationic polymers ranging from 0.1 g/L to 100 g/L.

* * * * *